United States Patent
Liebschner et al.

(10) Patent No.: US 10,842,377 B2
(45) Date of Patent: Nov. 24, 2020

(54) SYSTEM AND METHOD FOR INTRA-BODY COMMUNICATION

(71) Applicants: Michael Liebschner, Pearland, TX (US); Lin Zhong, Houston, TX (US); Mimi W. Zhang, Houston, TX (US); Michael S. Cordray, Houston, TX (US)

(72) Inventors: Michael Liebschner, Pearland, TX (US); Lin Zhong, Houston, TX (US); Mimi W. Zhang, Houston, TX (US); Michael S. Cordray, Houston, TX (US)

(*) Notice: Subject to any disclaimer, the term of this patent is extended or adjusted under 35 U.S.C. 154(b) by 466 days.

(21) Appl. No.: 15/706,228

(22) Filed: Sep. 15, 2017

(65) Prior Publication Data

US 2018/0070821 A1    Mar. 15, 2018

Related U.S. Application Data

(63) Continuation of application No. 12/602,469, filed as application No. PCT/US2008/066345 on Jun. 9, 2008, now abandoned.
(Continued)

(51) Int. Cl.
*A61B 5/00* (2006.01)
*A61B 5/024* (2006.01)
(Continued)

(52) U.S. Cl.
CPC .......... *A61B 5/0002* (2013.01); *A61B 5/0028* (2013.01); *A61B 5/0051* (2013.01);
(Continued)

(58) Field of Classification Search
CPC ... A61B 5/0051; A61B 5/0028; A61B 5/0002; A61B 5/02438; A61B 5/4519; A61B 5/4528; H04B 13/005
See application file for complete search history.

(56) References Cited

U.S. PATENT DOCUMENTS

| | | | |
|---|---|---|---|
| 4,754,763 | A | 7/1988 | Domeland |
| 5,002,065 | A | 3/1991 | LaCourse et al. |

(Continued)

FOREIGN PATENT DOCUMENTS

| | | |
|---|---|---|
| WO | 2008154504 A2 | 12/2008 |
| WO | 2008154504 A3 | 12/2008 |

OTHER PUBLICATIONS

Chang Hee Hyoung et al., A novel system for intrabody communication: Touch-and-Play, 2006, IEEE (Year: 2006).*
(Continued)

*Primary Examiner* — Sean P Dougherty
(74) *Attorney, Agent, or Firm* — Conley Rose, P.C.; Rodney B. Carroll (57) ABSTRACT

A method comprising generating a mechanical signal in a mammal, the mechanical signal having a frequency no more than 50,000 Hz, transmitting the mechanical signal through the musculoskeletal system in the mammal, and sensing the mechanical signal from the musculoskeletal system. A method of triggering an internal event comprising generating a mechanical signal internal or external to a mammal, transmitting the signal through the musculoskeletal system of the mammal, detecting the mechanical signal, and triggering an event in response to the mechanical signal. A method of drug delivery comprising generating a mechanical signal internal or external to a mammal, transmitting the signal through the musculoskeletal system of the mammal, detecting the mechanical signal, and delivering the drug in response to the mechanical signal.

20 Claims, 7 Drawing Sheets

US 10,842,377 B2
Page 2

Related U.S. Application Data (60) Provisional application No. 60/942,905, filed on Jun. 8, 2007.

(51) Int. Cl.
*A61B 5/145* (2006.01)
*H04B 13/00* (2006.01)

(52) U.S. Cl.
CPC .......... *A61B 5/4839* (2013.01); *A61B 5/0008* (2013.01); *A61B 5/02438* (2013.01); *A61B 5/145* (2013.01); *A61B 5/14532* (2013.01); *A61B 5/4504* (2013.01); *A61B 5/4509* (2013.01); *A61B 5/4514* (2013.01); *A61B 5/4519* (2013.01); *A61B 5/4528* (2013.01); *A61B 5/4533* (2013.01); *H04B 13/005* (2013.01)

(56) References Cited

U.S. PATENT DOCUMENTS

| | | | | |
|---|---|---|---|---|
| 5,024,239 | A | 6/1991 | Rosenstein | |
| 5,117,835 | A | 6/1992 | Mick | |
| 5,156,154 | A | 10/1992 | Valenta, Jr. et al. | |
| 5,368,044 | A | 11/1994 | Cain et al. | |
| 5,433,211 | A | 7/1995 | Brammer et al. | |
| 5,458,130 | A * | 10/1995 | Kaufman | G01N 29/348 600/449 |
| 5,897,510 | A | 4/1999 | Keller et al. | |
| 5,935,078 | A * | 8/1999 | Feierbach | A61B 5/0028 128/903 |
| 6,021,162 | A * | 2/2000 | Gaboury | H04L 27/1563 375/242 |
| 6,223,018 | B1 * | 4/2001 | Fukumoto | H04B 5/00 379/55.1 |
| 6,234,975 | B1 | 5/2001 | McLeod et al. | |
| 6,733,451 | B2 | 5/2004 | Rabiner et al. | |
| 6,754,472 | B1 | 6/2004 | Williams et al. | |
| 6,847,844 | B2 | 1/2005 | Sun et al. | |
| 6,875,176 | B2 | 4/2005 | Mourad et al. | |
| 6,950,681 | B2 | 9/2005 | Hofmann | |
| 7,022,076 | B1 | 4/2006 | Kantorovich et al. | |
| 7,099,749 | B2 | 8/2006 | Voeller | |
| 7,206,423 | B1 * | 4/2007 | Feng | H04B 13/005 381/312 |
| 7,228,183 | B2 | 6/2007 | Sun et al. | |
| 7,307,544 | B2 * | 12/2007 | Kim | A61B 5/0031 340/870.07 |
| 7,435,232 | B2 | 10/2008 | Liebschner | |
| 7,480,492 | B2 | 1/2009 | Williams et al. | |
| 7,531,939 | B2 * | 5/2009 | Takiguchi | H04B 13/005 310/311 |
| 7,536,020 | B2 * | 5/2009 | Fukumoto | G06F 1/163 340/384.6 |
| 7,629,897 | B2 | 12/2009 | Koljonen | |
| 7,945,064 | B2 * | 5/2011 | O'Brien, Jr. | H04B 13/005 381/312 |
| 8,588,887 | B2 * | 11/2013 | Arneson | A61B 5/0002 600/407 |
| 9,149,577 | B2 * | 10/2015 | Robertson | A61B 5/0006 |
| 9,308,377 | B1 * | 4/2016 | Schaefer | A61N 1/37205 |
| 2001/0041845 | A1 | 11/2001 | Kim | |
| 2002/0095087 | A1 | 7/2002 | Mourad et al. | |
| 2003/0199784 | A1 | 10/2003 | Lenhardt | |
| 2004/0167674 | A1 * | 8/2004 | Voeller | G01B 21/26 700/279 |
| 2006/0018488 | A1 * | 1/2006 | Viala | H04R 1/1091 381/74 |
| 2007/0105072 | A1 * | 5/2007 | Koljonen | H04R 1/083 434/112 |
| 2010/0004624 | A1 | 1/2010 | Hunter | |
| 2010/0238955 | A1 * | 9/2010 | Sung | H04B 13/005 370/498 |
| 2010/0305437 | A1 * | 12/2010 | Liebschner | A61B 5/0002 600/437 |

OTHER PUBLICATIONS

Marc Wegmueller et al., Galvanical Coupling for Data Transmission through the Human Body, 2006, IMTC (Year: 2006).*

Foreign communication from a related counterpart application—International Search Report and Written Opinion, PCT/US2008/066345, dated Jan. 6, 2009, 9 pages.

Foreign communication from a related counterpart application—International Preliminary Report on Patentability, PCT/US2008/066345, dated Dec. 11, 2009, 6 pages.

Liebschner, M. A. K., et al., "Osteo-conduct: ubiquitous wireless body-area communication and interfacing network," International Journal of Medical Implants and Devices, 2007, vol. 2, No. 1, 4 pages, Medical and Engineering Publishers, Inc.

Liu, Zicheng, et al., "Leakage model and teeth clack removal for air- and bone-conductive integrated microphones," Proceedings of the IEEE International Conference on Acoustics, Speech, and Signal Processing, 2005, Mar. 18-23, 2005, pp. 1093-1096 and cover sheet, IEEE.

Provisional patent application entitled "System and method for intra-body communication," by Michael Liebschner, et al., filed Jun. 8, 2007 as U.S. Appl. No. 60/942,905.

Shih, Eugene, et al., "Wake on wireless: an event driven energy saving strategy for battery operated devices," MOBICOM, Sep. 23-26, 2002, 12 pages, ACM.

Stenfelt, Stefan, et al., "Transmission properties of bone conducted sound: measurements in cadaver heads," Journal of the Acoustical Society of America, Oct. 2005, vol. 118, No. 4, pp. 2373-2391, Acoustical Society of America.

Tatarinov, Alexey, et al., "Use of multiple acoustic wave modes for assessment of long bones: model study," Ultrasonics, Aug. 2005, vol. 43, No. 8, pp. 672-680, Elsevier B. V.

Zhong, Lin, et al., "OsteoConduct: wireless body-area communication based on bone conduction," BodyNets, Proceedings of the ICST 2nd Annual International Conference on Body Are Networks, Jun. 2007, pp. 1-8.

Fukumoto, Masaaki, "A finger-ring shaped wearable HANDset based on bone-conduction," Proceedings of the 2005 Ninth IEEE International Symposium on Wearable Computers (ISWC' 05), 2005, 4 pages, IEEE Computer Society.

Nicholson, Patrick H. F., et al., "Guided ultrasonic waves in long bones: modelling, experiment and in vivo application," Physiological Measurement, 2002, vol. 23, cover page, pp. 755-768, Institute of Physics Publishing.

Sakaguchi, Takefumi, et al., "Inner head acoustic field for bone-conducted sound calculated by finite-difference time-domain method," Japanese Journal of Applied Physics, May 2002, vol. 41, part 1, No. 5B, pp. 3604-3608, The Japan Society of Applied Physics.

Stenfelt, Stefan, et al., "Vibration characteristics of bone conducted sound in vitro," Journal of the Acoustical Society of America, Jan. 2000, vol. 107, No. 1, pp. 422-431, Acoustical Society of America.

Sohmer, Haim, et al., "Bone conduction experiments in humans—a fluid pathway from bone to ear," Hearing Research, 2000, vol. 146, pp. 81-88, Elsevier Science B.V.

Yang, Dan, et al., "The study of digital ultrasonic bone conduction hearing device," Proceedings of the 2005 IEEE Engineering in Medicine and Biology 27th Annual Conference, Shanghai, China, Sep. 1-4, 2005, pp. 1893-1896, IEEE.

Tamer Mohamed & Lin Zhong, TeethClick: Input with Teeth Clacks (2007), available at http://wayback.archive.org/web/20060515000000*/http://www.ruf.rice.edu/~mobile/publications/teethclick06mohamed.pdf (earliest modified Jan. 17, 2007. Last visited Jan. 6, 2012 at 3:31 pm EST).

Tamer Mohamed & Lin Zhong, Clackdemo.wmv (2007) available at http://wayback.archive.org/web/query?q=type%3Aurlquery+requestexactscheme%3Ayes+uri%3Ahttp%3A%2F%2Fwww.ruf.rice.edu%3A80%2F%7Emobile2Fpublications%2Fclackdemo.wmv&count=20000&start_page=1 (earliest modified Jan. 17, 2007. Last visited Jan. 6, 2012 at 3:31 pm EST).

Office Action of U.S. Appl. No. 12/602,469, dated Jan. 23, 2012, 36 pages.

Office Action of U.S. Appl. No. 12/602,469, dated Apr. 4, 2013, 30 pages.

(56) References Cited

OTHER PUBLICATIONS

Final Office Action of U.S. Appl. No. 12/602,469, dated Oct. 9, 2013, 11 pages.
Advisory Action of U.S. Appl. No. 12/602,469, dated Dec. 13, 2013, 3 pages.
Office Action of U.S. Appl. No. 12/602,469, dated Jan. 28, 2014, 12 pages.
Final Office Action of U.S. Appl. No. 12/602,469, dated Jun. 24, 2014, 15 pages.
Examiner's Answer in response to appeal brief of U.S. Appl. No. 12/602,469, dated Oct. 6, 2015, 29 pages.
Decision on appeal of U.S. Appl. No. 12/602,469, dated Jul. 17, 2017, 26 pages.

* cited by examiner

FIG. 1

(a) Test platform with the electromagnetic shaker (b) Test platform with a subject's forearm in (Shaker was not present)

| Source → Destination | Bit error rate (BER) (%) | |
|---|---|---|
| | M | F |
| Wrist to Ear 1 → 3 | 6.7 | 13.8 |
| Wrist to Lower back 1 → 2 | 2.1 | 0.3 |
| Lower back to Wrist 2 → 1 | 0.5 | 18.7 |
| Lower back to Ear 2 → 3 | 12.3 | 4.3 |
| Average | 5.4 | 9.3 |

SYSTEM AND METHOD FOR INTRA-BODY COMMUNICATION

CROSS-REFERENCE TO RELATED APPLICATIONS

This application is a continuation of and claims priority to U.S. patent application Ser. No. 12/602,469 filed Apr. 30, 2010, published as U.S. Patent Application Publication US 2010/0305437 A1 and entitled "System and Method for Intra-Body Communication," which is a filing under 35 U.S.C. 371 of International Application No. PCT/US2008/066345 filed Jun. 9, 2008, entitled "System and Method for Intra-Body Communication," claiming priority of U.S. Provisional Patent Application No. 60/942,905 filed Jun. 8, 2007, which applications are incorporated by reference herein in their entirety.

BACKGROUND

Field of the Invention

This invention relates generally to the field of body area networks, in particular intra-body communication. More specifically, the invention relates to a system and method of intra-body communication using the musculoskeletal system of a mammal.

Background of the Invention

Acoustic sound wave propagation through bone tissue is a widely-used technique in evaluating bone mechanical properties, specifically predicting bone elastic properties through speed-of-sound measurements. This is particularly critical for diagnosing and monitoring the progression of osteoporosis as well as assessing the extent of fracture healing in long bones and monitoring drug treatment. Such systems measure speed of sound and/or broadband attenuation coefficient and correlate these parameters to bone properties. Nevertheless, these devices operate in the ultrasound range with very limited penetration depth into hard connective tissues such as bones. Reliable sound wave propagation using ultrasound is only possible within a few millimeters.

In an alternative approach, recent studies have suggested the applicability of bone-conducted sound waves in hearing aids for the severely hearing disabled. Acoustic wave bone conduction hearing aids have been found capable of supporting frequency discrimination and speech detection for hearing impaired and profoundly deaf subjects. These systems capture the surrounding/external analog acoustic signals within the audible range, amplify the signals and propagate the same analog frequency content to the inner ear. These systems are generally placed at the outer ear but can also be finger worn. The skull is used to propagate the sound waves from the outer ear a relative short distance to the inner ear without modification of the analog signal.

Reliable acoustic wave propagation across multiple bones, however, can only be achieved in the low-frequency range, typically around the resonance frequency of the tissue. Resonance of the tissue has the advantage that the whole tissue is excited, instead of a few millimeters as with ultrasound. The downside is the lower data transfer rate compared to high frequency techniques if serial data communication is applied. Several non-RF body-area communication techniques have been proposed that use the body's own electrical field. However existing techniques suffer from an extremely limited range, due to the low and uneven electrical conductivity of the human body. Numerous works exist on the vibration characteristics of various human bones, especially human skulls for the application in hearing aid. However, none of them considered the use of musculoskeletal conduction for body-area communication and interfacing.

Consequently, there is a need for systems and methods of intra-body communication using musculoskeletal mechanical conduction.

BRIEF SUMMARY

The disclosed methods and systems utilize wireless transmittance of a mechanical signal through the musculoskeletal system of a mammal. Mechanical signals may be generated through engineered devices or by the user and transmitted through the user's own musculoskeletal system to other anatomic regions or to another user. Further aspects and features of embodiments of the methods and systems will be discussed below.

In an embodiment, a method comprises generating a mechanical signal in a mammal. The method also comprises transmitting the mechanical signal through the musculoskeletal system in the mammal. The method further comprises sensing the mechanical signal from the musculoskeletal system.

In another embodiment, a method of communicating with an implanted device (e.g. drug delivery system) comprises generating a mechanical signal internal or external to a mammal. Furthermore, the method comprises transmitting the signal through the musculoskeletal system of the mammal. The method also comprises detecting the mechanical signal. Additionally, the method comprises delivering the drug in response to the mechanical signal.

In one embodiment, a method of monitoring one or more body parameters comprises generating a mechanical signal internal or external to a mammal. The mechanical signal is encoded with data corresponding to the one or more body parameter. The one or more body parameters comprise but are not limited to blood pressure, ECG, heart rate, body temperature, glucose level, bone integrity or combinations thereof The method further comprises transmitting the signal through the musculoskeletal system of the mammal. In addition, the method comprises detecting the mechanical signal and decoding the mechanical signal to monitor the one or more body parameters. The sensor component may work autonomously or is in two-way communication with the receiver unit.

In an embodiment, a method of identifying a mammal comprises generating a mechanical signal internal or external to the mammal. The method also comprises transmitting the signal through the musculoskeletal system of the mammal. The method additionally comprises detecting the mechanical signal. Moreover the method comprises comparing the mechanical signal to a reference signal to identify the mammal.

In another embodiment, a method of diagnosing an injury in a mammal comprises generating a mechanical signal internal or external to the mammal. The method further comprises transmitting the signal through the musculoskeletal system of the mammal. Furthermore, the method comprises detecting the mechanical signal and comparing the mechanical signal to a reference signal to diagnose the injury, the reference signal wherein the injury comprises a fracture, a tear, a trauma, internal bleeding, or combinations thereof The reference signal may be drawn from a data base or the contralateral side of the person being tested.

In one embodiment, a system for intra-body communication in a mammal comprises a mechanical signal generator coupled to the body of the mammal. The system also comprises a receiver capable of detecting a mechanical signal (e.g., low frequency signal) generated from said mechanical signal generator. The method further comprises transmitting data in a modulated format. The intra-body communication can be further extended through physical contact to another individual, for example but not limited to through a handshake.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

As used herein, "intra-body communication" may refer to internal communication within a single mammalian body. However, sensors and components can be internally or externally to the individual.

As used herein, "musculoskeletal system" refers to the portions of a mammal pertaining to the bone and joints and surrounding soft tissue such as connective tissue, muscle, ligaments and cartilage.

As used herein, a "mechanical signal" refers to vibrations or signals that are generated from a mechanical/physical input (e.g. shaking, tapping, vibrating, etc.) and are non-electrostatic or optical in nature.

As used herein, "mammal" refers to humans and other mammalian animal species.

DETAILED DESCRIPTION OF THE PREFERRED EMBODIMENTS

Figure 1:
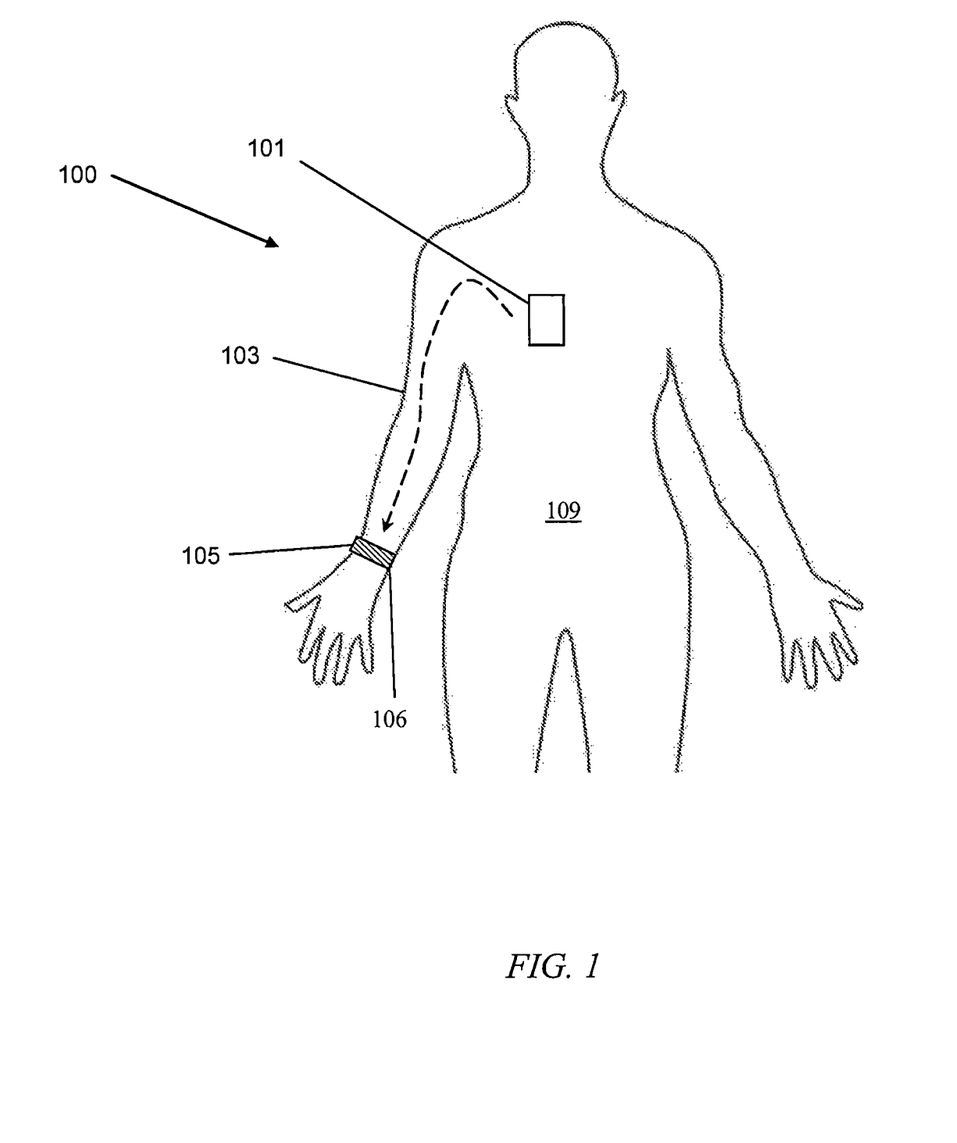
FIG. 1 illustrates an embodiment of a method and system for intra-body communication.
Figure 2:
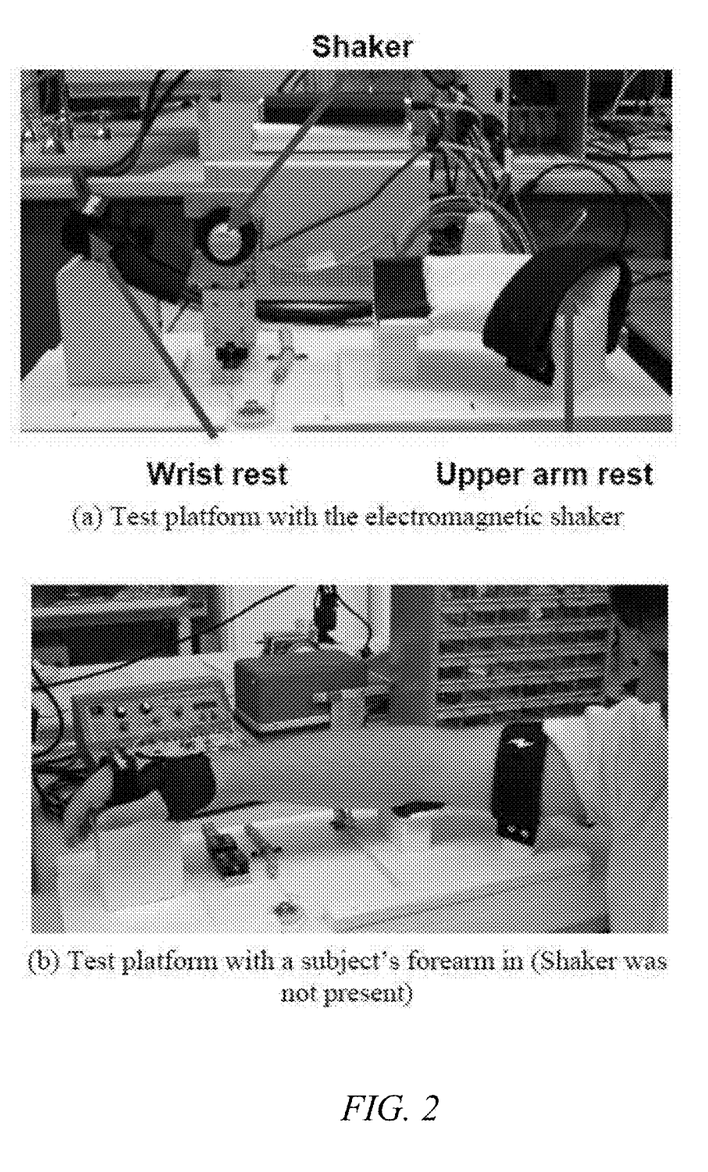
FIG. 2 illustrates an experimental setup for an embodiment of the system.

As FIG. 1 illustrates, embodiments of an intra-body communication system 100 may comprise a stimulator 101 that produces mechanical excitations yielding vibrations or a signal, a portion 103 of the mammalian musculoskeletal system that conduct the vibrations or signals, and a receiver 106 or sensor 105 that detects the vibration. In another embodiment, the direction of communication is reversed. In another embodiment, only one of the components is external to the individual while the other is internal in the body. In another embodiment, both receiver 106 and transmitter are internal. In another embodiment, the method may be extended across more than one individual. As used herein, a mechanical vibration or signal may refer to any vibration or signal that is transmitted non-electrically. In other words, the vibration or signal does not rely on electromagnetic or electrostatic signals such as radio waves for transmittal. In embodiments, bone conduction may be excited externally. For example, vibrators on mobile phones can be used to generate frequency patterns in the lower audible range. In an embodiment, the stimulator may be an electro-mechanical stimulator, electro-magnetic stimulator or a piezoelectric stimulator. Low-frequency vibration patterns are commonly generated by either vibration motors or electromagnetic shakers. In vibration motors, the amplitude and frequency may be coupled through a mechanical link to an eccentric weight. Increasing the motor speed may also increase the excitation. Electromagnetic stimulators or shakers and piezo-electric stimulators allow for a separation between amplitude and frequency. Through power limiting components a flat power spectrum of the shaker can be achieved, allowing robust data communication between different devices at alternate frequency ranges.

In other embodiments, the user 109 may be the stimulation or vibration source. A user 109 can easily produce bone vibrations, e.g., through teeth clicks and finger snaps. Such user initiated excitation can be readily used for interfacing with the embodiments of the system. Furthermore, a user 109 may tap the skin or make a motion with a limb to generate a mechanical vibration.

The stimulator 101 may be placed in any location in or on the body. Thus, embodiments of the system 100 enable wireless body-area communication based on mechanically excited bone conduction inside the human musculoskeletal system. Example of locations for placing stimulator 101 include without limitation, wrist, throat, head, heart, lungs, skull, ankle, leg, etc. Embodiments of the system 100 are intended as a secure, reliable, low-power, low cost, and low-data rate alternative to existing RF technologies. Measurements and theoretical analysis have shown that ultra low-power (i.e. <1 mW) excitation is enough for fairly reliable communication (<10% bit error rate), without being noticeable to the user 109. Adding error compensation methods may reduce that error.

The receiver 106 or sensor 105 may comprise any suitable sensor, which is sensitive enough to detect vibrations or signals from the body. Alternatively, one or more sensors 105 may be used. Examples of sensors that may be used include without limitation, a microphone, an accelerometer, or combinations thereof In a specific embodiment, the sensor 105 is a MEMS based three-axis accelerometer. The sensor 105 may be a low power sensor, thus making the system extremely power efficient. In embodiments, the sensors may use power in the range of between about 1 mW and about 100 mW, alternatively between about 2 mW and 50 mW, alternatively between about 0.1 mW and about 2 mW. Receiver 106 or sensor 105 may be located or disposed within the body or external to the body. In one embodiment shown in FIG. 5, the sensor 105 may be worn on the wrist much like a wristwatch.

In some embodiments, system 100 may further comprise charge converters and amplifiers coupled to the sensor 105 and/or the stimulator 101. Any charge converters and amplifiers known to those of skill in the art may be used.

Initial investigation and experimental results have shown that embodiments of the system have the potential to interconnect body-worn or implanted devices and provide users with alternative ways to interact with them. In particular, system 100 may be free of radiation and require extremely low power to maintain a connection and transfer data. Another advantage of the disclosed systems and methods is the two-way exchange of information between implanted devices and/or receivers.

In an embodiment, system 100 may interact with body-worn devices in a hand-free fashion, e.g., to answer a phone call through the Bluetooth headset by a teeth click. Furthermore, the system 100 may manage a power-hungry RF wireless body-area connection as a secondary ultra-low power channel, or wake-on-vibration. For example, a Bluetooth connection between a headset and a cell phone can be shutdown between calls and be reestablished upon a request from the cell phone through embodiments of the system. An additional advantage of system 100 is that body-area data communication may be maintained in a hostile environment, where radio frequencies are likely to be jammed or insecure.

In embodiment of a method of intra-body communication, a stimulator 101 initiates or generates a mechanical vibration in a user 109. As discussed above, the stimulator 101 may be placed at any location in or on the body of the user 109. The mechanical signal is transmitted through the musculoskeletal system of the user 109. In embodiments, the mechanical signal is encoded using frequency and/or amplitude modulation. In this way, the mechanical signal may carry data such as blood pressure, heart rate, or other body parameters to receiver 106. It is emphasized that the disclosed methods and systems are different than ultrasound techniques, which rely on the reflection of ultrasonic high frequency sound waves for imaging purposes. In an embodiment, the mechanical signal or vibration is generated at a frequency from about 5 Hz to about 50,000 Hz, alternatively from about 10 Hz to about 10,000 Hz, alternatively from about 50 Hz to about 5,000 Hz. Preferably, the mechanical signal is a signal having a frequency no more than about 20 kHz. That is, the mechanical signal is generally below frequencies considered to be in the ultrasound range.

The mechanical signal may be transmitted through the bones and cartilage of the user 109 or mammal. A sensor 105 or receiver 106 then detects the mechanical signal. In addition, receiver 106 may decode or demodulate the mechanical signal to receive the data encoded within the mechanical signal. In response to the detected signal, sensor 105 may initiate an action (i.e. drug delivery), output data received from stimulator 101, activate an alarm, send information back to origin using the same technique in reverse, etc.

Accordingly, it is envisioned that the disclosed systems and methods may be used in numerous applications. In one embodiment, the method and system may be used for drug release applications. For example, an internal drug dispensing device may be implanted within a patient (e.g. user 109). Sensor 105 may be coupled to the drug dispensing device. In response to a mechanical signal (e.g. teeth click or a signal generated from a stimulator 101) sensor 105 may detect signal and instruct drug dispensing device to release drugs into the body. Sensors may detect the effectiveness of the drug and allow the user 109 to trigger another dose release after communication with the stimulator. Such systems may allow for patient targeted treatment. This may be particularly useful in chronically ill patients, diabetic patients or patients undergoing cancer treatment.

In another application, the disclosed systems and methods may be used in health monitoring. For example, a biosensor may measure a body parameter such as without limitation, blood sugar, body temperature, oxygen saturation, heart rate, and the like. The biosensor may send this data to stimulator 101 to transmit the data through the musculoskeletal system of the user 109. Receiver 106 may detect and decode signal and output the data received to an output display (e.g. LCD screen) or may store data on storage medium such as without limitation, a flash card, hard drive, or other devices known to those of skill in the art. The information, raw or processed, may then be forwarded to a base station (e.g. computer), a smart phone, or cell phone. Depending on the complexity of the system setup the information may be forwarded directly to a physician's office or nurses station, first responders, or other qualified personnel.

Embodiments of the systems and methods may also be used for identification purposes. Without being limited by theory, it is believed that each individual will have different transmission or conduction rates of mechanical signals through the musculoskeletal system. Furthermore, as a mechanical signal pass through each person's musculoskeletal system, the signal may be distorted in a unique way or pattern which may be used to identify an individual. As such, in an embodiment, a stimulator may be placed on the skin of a suspect or person to be identified. A mechanical signal may be generated by the stimulator 101 and the receiver 106, placed on a different or the same area of the body, may detect the generated mechanical signal after passing through the person's musculoskeletal system. Using pattern recognition, the receiver 106 may positively or negatively identify the tested individual according to the signal detected. Alternatively, an individual may be already implanted with one of the components.

In a further application, embodiments of the systems and methods could be used in medical diagnosis. Specifically, a medical emergency professional may be able to diagnose conditions in the field such as without limitations, ligament tears, cartilage damage or hairline fractures and bone damage. Normally, a patient may have to wait until a full x-ray, computed tomography or magnetic resonance imaging dataset has been taken in order to for a proper diagnosis to be made. Without being limited to theory, it is believed that an injury to a healthy bone or ligament may have distorted a mechanical signal in one way. Or a healthy bone or ligament may transmit a mechanical signal differently than injured tissue. Using an embodiment of the disclosed system, differences in the signal or rate of transmission may alert a professional of a possible fracture, tissue damage or tissue injury. In other embodiments, damage to organs or other tissue types may also be diagnosed besides musculoskeletal injuries. In other embodiments, damage or loosening of implants, functional parameters of implants or the quality of the implant tissue interface may also be diagnosed.

In yet another application, embodiments of the disclosed methods and systems may be used for assisting handicapped individuals. For example without limitation, a handicapped person could click his or her teeth to activate a cell phone or other device strapped to his or her body (e.g. wrist, ankle, etc). In such applications, the receiver may also be a wireless transmitter enabling the user person to operate external devices through teeth clicks or other rudimentary motions.

To further illustrate various illustrative embodiments of the present invention, the following examples are provided.

EXAMPLE 1

A reaction-type low-power electromagnetic shaker was built to generate mechanical signals through dynamic forces. This type of shaker offers a lightweight and compact configuration, ideal for miniaturization. In addition, such shakers are designed for operation over a very wide range of frequencies. Bone-conduction was detected using accelerometers with coupled amplifiers. An ultra low-power MEMS based three-axis accelerometer from Kionix was held against the receiving body location as the receiver. A LabVIEW program controlled the entire system. Binary input sequences were modulated into different frequencies to drive the electromagnetic shaker. The same program received the signal from the accelerometers and demodulated the signal. The received bit sequence was then compared to the input sequence to calculate accuracy. In a first testing series, human subjects were exposed to a localized low-frequency excitation signal pattern at the wrist and receivers were placed at the lower back or the skull. At a second series, the excitation source was at the lower back and receivers measured the response at the wrists and the skull.

Human subjects were recruited and consented to this study. For the first testing series, subjects placed their forearm in the custom built testing jig. The exciter was placed against the distal ulna with a constant pre-load of 20 N. Multiple tri-axial MEMS accelerometers were placed along the elbow, shoulder, skull and lower back and attached to the skin through adhesive. Reliable signal transmission was monitored after varying power consumption of the system. Subsequently, the anatomic site at which the excitation is applied was altered and the test repeated. Bit error rate (BER) based on the 2048 random bit combinations were calculated and reported.

ASK (amplitude shift-keying) and FSK (frequency shift-keying) for data communication was examined, primarily due to their simplicity. A LabVIEW program was developed to encode the raw bits into modulated signals to control the input voltage of the electromagnetic shaker, as described above. In FSK modulation, on and off frequencies are chosen for constant amplitude. The range of on frequencies used was between the lower shaker bound of 10 Hz and a selected upper bound of 2000 Hz, with the off frequency being defined in terms of the on frequency interval. The receiver determined the frequency using LabVIEW's built-in Buneman frequency estimator. For ASK modulation, the input signal frequency was held constant, while different amplitude values were assigned to a chosen bit pattern. A 0-0.001 g off amplitude of the acceleration signal and 0.1-1.0 g on amplitude of the acceleration signal was applied. The unit g represented the earth gravitational acceleration of 9.81 m/s^2.

Figure 3:
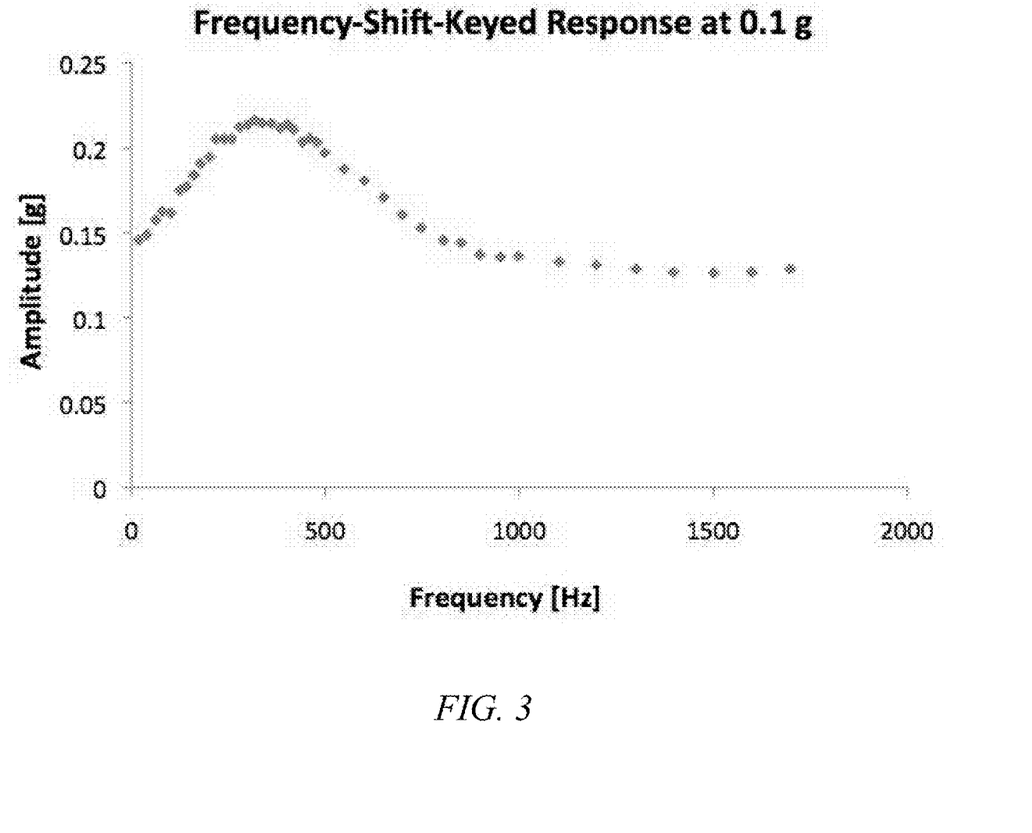
FIG. 3 illustrates Frequency-Shift-Keyed response at 0.1 g signal amplitude of an embodiment of the system.

FSK consistently outperformed ASK in accuracy when similar vibration forces were employed. ASK suffered more from the muscle attenuation and changes in muscular contraction. The demodulator of FSK was much simpler and more robust than that of ASK. Therefore, we focused on the properties and performance of FSK in the follows. Secondly, 300-350 Hz was best for FSK for the arm bone examined. Frequency sweeps were performed over the range of 10-2000 Hz. The frequency range between 300-350 Hz demonstrated the least amplitude attenuation, as showed in FIG. 3. Our later experiments showed this frequency range also works well for other part of the skeleton system and for other subjects.

Figure 4:
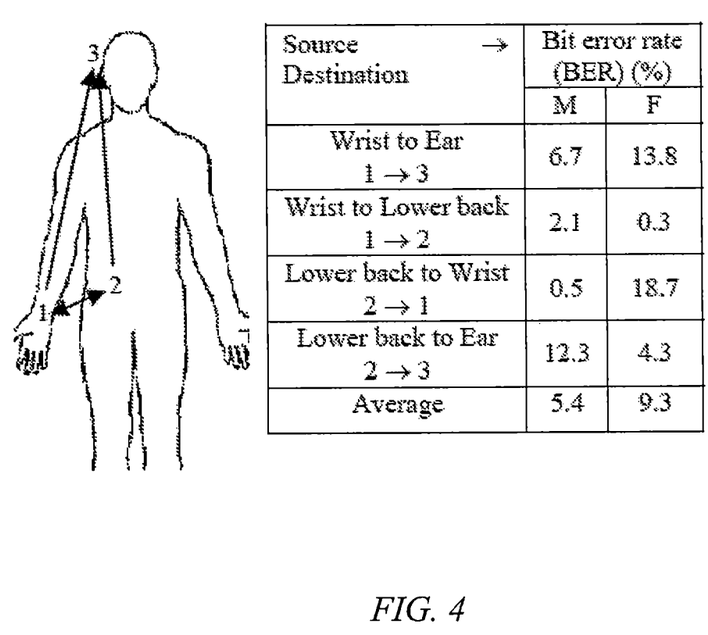
FIG. 4 shows results of experiments run at transmitter locations at the wrist (1) and lower back (2) and receiver locations of wrist (1), lower back (2), and behind the ear (3)

FIG. 4 summarizes the measurement results. The experimental system achieved <10% bit error rate without any error correction. This result was quite exciting because all four links involve multiple bones and several joints. Second, the performance was asymmetric. For example, the female subject had much lower BER from the wrist to the lower back than from the lower back to the wrist. Thirdly, the difference between subjects was considerable. On average the male subject accumulated a much lower BER. Causes of that discrepancy will need to be further investigated.

EXAMPLE 2

Portable Receiver

Figure 5:
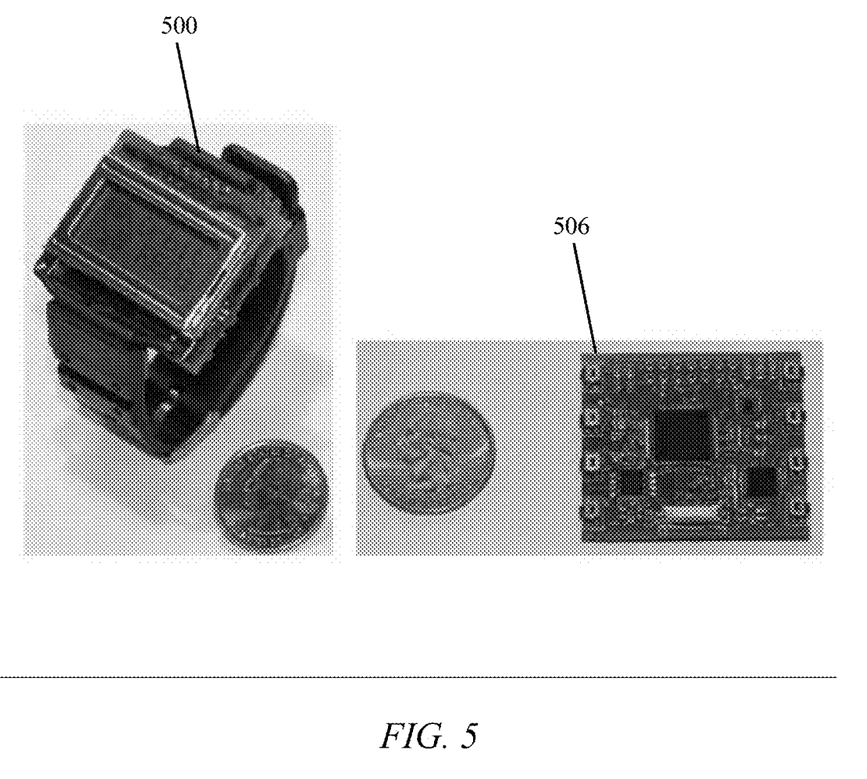
FIG. 5 shows a picture a wrist-based sensor for use with embodiments of the system and method.

An ultra-low power receiver 506 was built in the form factor of a wrist-watch 500, which is shown in FIG. 5. It employed the same ultra-low power three-axis accelerometer used in Example 1 and an ultra-low power microcontroller (MSP430) from Texas Instruments. The active power consumption during receiving was below 5 mW. The device is capable of activating sequences and programs after minimal wrist flicking. In addition, the current version allows Bluetooth communication with cell phones for data communication outside the proposed system. In embodiments, the wristwatch 500 functions as base station and communication link to other body worn devices and external mobile systems.

EXAMPLE 3

Teeth Clicking

Figure 6:
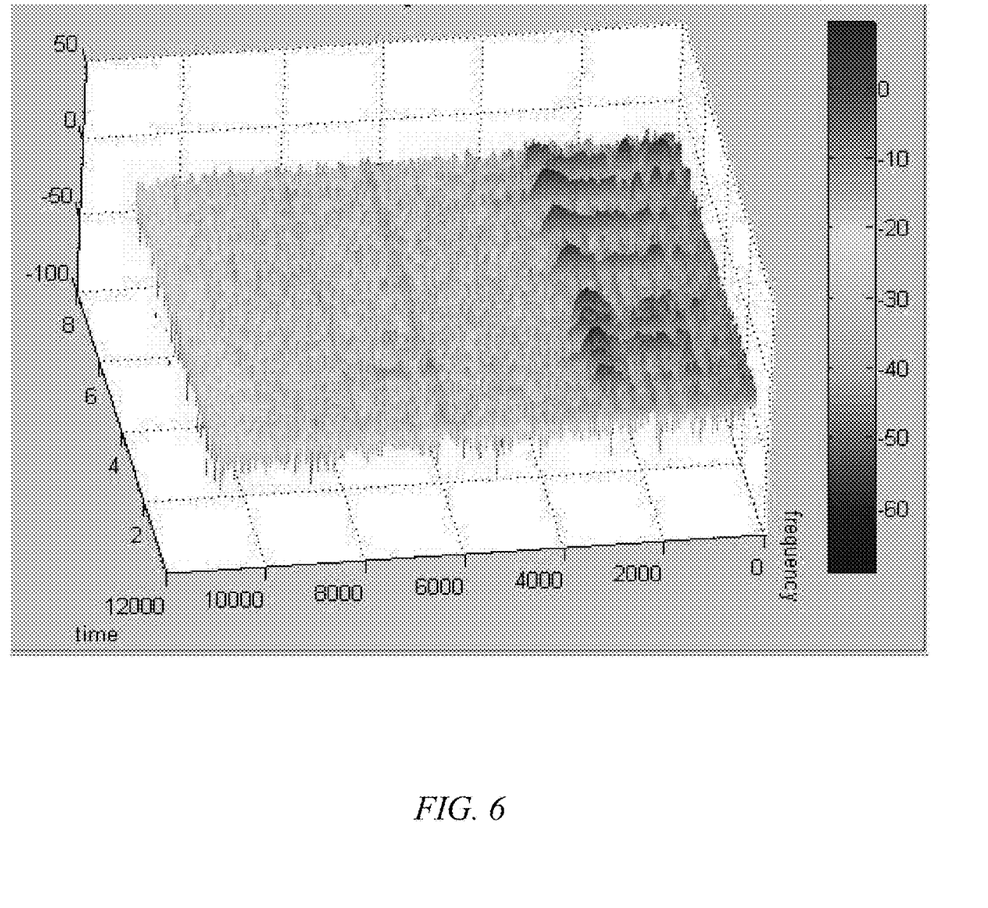
FIG. 6 shows a plot spectrum vs. time for bone-conduction signal of a series of deliberate teeth clicks.
Figure 7:
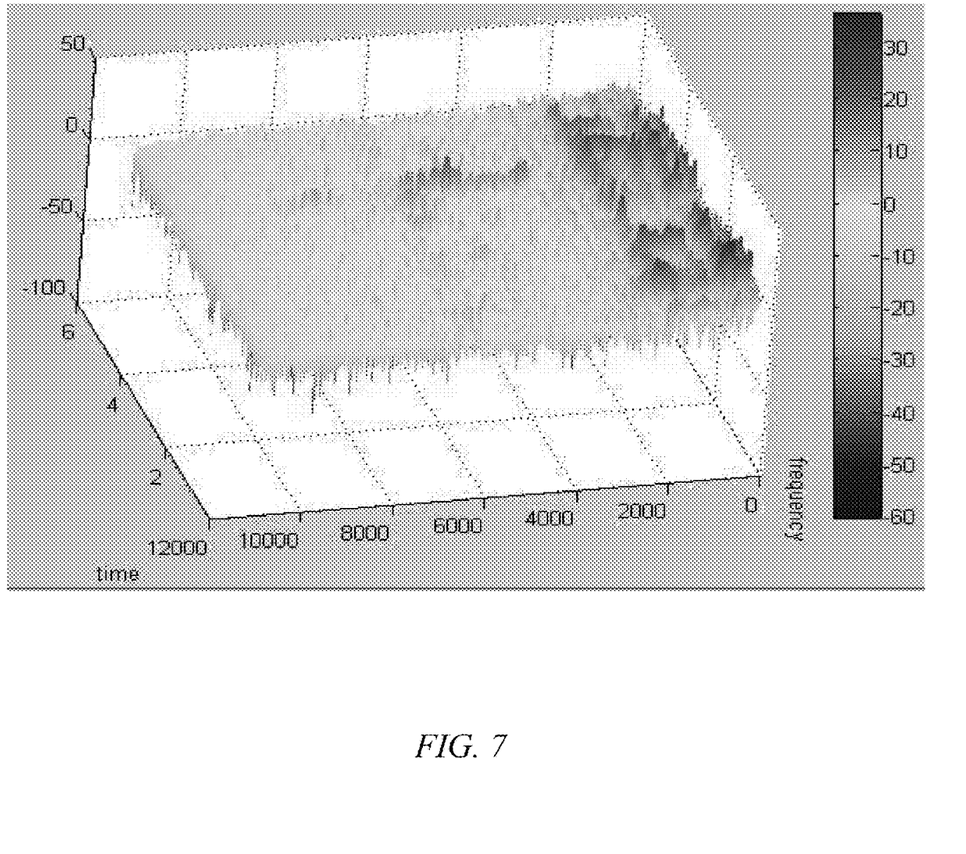
FIG. 7 shows a spectrum vs. time for bone-conduction signal of speech.

The bone-conduction signal of teeth clicks is characterized by high energy in spectrum above 2000 Hz, but low energy below it. FIG. 6 shows the time-spectrum of the bone conduction signal of several teeth clicks. The spectrum of the bone-conduction signal of speech, as shown in FIG. 7, is almost the opposite. It is characterized by high energy in spectrum below 2000 Hz, but low energy above it. This dramatic difference is introduced because the skin and skull inherently are a much lower low-pass filters to acoustic signals than the bone tissue due to vibration incurred by teeth clicks. This forms the basis for our algorithm to detect teeth clicks.

For low-power and real-time implementation, an algorithm was designed based on the property of the bone-conduction signal. The algorithm examined the energy densities in the lower and higher spectral ranges of the bone-conduction signal. High energy density in the lower spectral range indicated the existence of speech, while a sudden increase in the energy density in the higher spectral range indicated the occurrence of a teeth click. A deliberate teeth click was detected if a teeth click occurred without the presence of speech. The experimental implementation was based on standard speech signal processing. The bone-conduction signal was sampled and divided into overlapping frames. In the implementation, each frame was about 23.3 ms and adjacent frames are about 22 ms apart. For each frame, the Fast Fourier Transform (FFT) Signal was calculated to obtain the frequency spectrum. The "low" spectral range was between 0 and 2750 Hz, while the "high" spectral range was between 1875 and 5500 Hz. For the nth frame, the energy densities were calculated in the low and high spectral ranges, denoted as $A_n$ and $B_n$, respectively. Records were kept of the average energy density of silence, U. If $B_n$ was considerably larger than $B_{n-1}$ and $B_{n+1}$, the algorithm declared that a teeth click was detected. For accidental teeth clicks, $A_{n-1}$ and $A_{n+1}$ were large due to the presence of speech. Therefore, the algorithm declared that a deliberate teeth click was detected if and only if Bn is considerably larger than $B_{n-1}$ and $B_{n+1}$ and $A_{n-1}$ and $A_{n+1}$ is on the same level as the U. Let $C_n$ be the Boolean logic that evaluates whether a deliberate teeth click is detected for the nth frame. It can be formulated as $$C_n = [(B_{n-1} + \text{offset} < B_n)] \text{ and } [(B_{n+1} + \text{offset} < B_n)] \text{ and } [A_{n-1} \leq (U + \text{offset})] \text{ and } [A_{n+1} \leq (U + \text{offset})]$$

where offset is empirically set to 5 dB. It is important to note that while the algorithm is based on the generic property of the bone-conduction signal, its implementation is highly dependent on the property of the transducer (e.g. throat microphone). In this implementation, the low and high spectral ranges as well as the offset were empirically determined by examining the bone-conduction spectrum.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

REFERENCES (HEREIN INCORPORATED BY REFERENCE IN THEIR ENTIRETIES FOR ALL PURPOSES)

1. Nicholson, P. H. F., Moilanen, P., Karkkainen, T., Timonen, J. and Cheng, S. Guided ultrasonic waves in long bones: modelling, experiment and in vivo application. *Physiol. Meas*, 23 (4). 755-768.
2. Tatarinov, A., Sarvazyan, N. and Sarvazyan, A. Use of multiple acoustic wave modes for assessment of long bones: Model study. *Ultrasonics*, 43 (8). 672-680.
3. Sakaguchi, T., Hirano, T., Watanabe, Y., Nishimura, T., Hosoi, H., Imaizumi, S., Nakagawa, S. and Tonoike, M. Inner Head Acoustic Field for Bone-Conducted Sound Calculated by Finite-Difference Time-Domain Method. *Jpn. J. Appl. Phys*, 41. 3604-3608.
4. Yang, D., Xu, B., Wang, X. and Jia, X., The Study of Digital Ultrasonic Bone Conduction Hearing Device. in *Proceedings of the Annual International Conference of the IEEE Engineering in Medicine and Biology Society*, (2005), 1893-1896.
5. Williams, L., Vablais, W. and Bathiche, S. N. Method and Apparatus for Transmitting Power and Data using the Human Body. Paten, U.S. ed., Microsoft Corporation, Redmond, Wash., USA, 2004, 15.
6. Sun, M., Sclabassi, R. J. and Mickle, M. H. Method of data communication with implanted device and associated apparatus. Patent, U.S. ed., University of Pittsburgh of the Commonwealth System of Higher Education, Pittsburgh, Pa., USA, 2005, 14.
7. Sohmer, H., Freeman, S., Geal-Dor, M., Adelman, C. and Savion, I. Bone conduction experiments in humans-a fluid pathway from bone to ear. *Hear Res*, 146 (1-2). 81-88.
8. Stenfelt, S. and Goode, R. L. Transmission properties of bone conducted sound: measurements in cadaver heads. *J Acoust Soc Am*, 118 (4). 2373-2391.
9. Stenfelt, S., Håkansson, B. and Tjellström, A. Vibration characteristics of bone conducted sound in vitro. *The Journal of the Acoustical Society of America*, 107. 422.
10. Fukumoto, M., A finger-ring shaped wearable handset based on bone-conduction. in *Proceedings of IEEE International Symposium on Wearable Computers*, (2005), 10-13.
11. Shih, E., Bahl, P. and Sinclair, M. J. Wake on Wireless: An Event Driven Energy Saving Strategy for Battery Operated Devices. *Proceedings of ACM MobiCom*.
12. Zicheng Liu et al, "Leakage model and teeth clack re-moval for air-and-bone conductive integrated microphones", Proc. IEEE Int. Conf. Acoustics, Speech & Signal Processing (ICASSP), Philadelphia, 2005.

What is claimed is:

1. A method comprising:
   a) generating, by a mechanical signal generator located internal or external to a mammal, an engineered mechanical signal comprising encoded data;
   b) transmitting the engineered mechanical signal through a musculoskeletal system of the mammal;
   c) sensing, by a receiver device, the engineered mechanical signal from the musculoskeletal system; and
   d) applying error compensation to a data sequence of the sensed mechanical signal.

2. The method of claim 1, further comprising:
   encoding, by a computer program before step a), raw bits of data into encoded data, wherein the computer program controls an input voltage of the mechanical signal generator to generate the engineered mechanical signal comprising the encoded data.

3. The method of claim 1, wherein the mechanical signal generator and the receiver device are each placed on an outer surface of the mammal.

4. The method of claim 1, wherein the engineered mechanical signal has a frequency ranging from about 10 Hz to about 20,000 Hz.

5. The method of claim 1, wherein c) comprises using a transducer to convert the engineered mechanical signal into an electrical signal.

6. The method of claim 1, wherein the encoded data comprises a sequence of ON frequencies and OFF frequencies, wherein each ON frequency is generated in an ON frequency interval, wherein the ON frequency interval defines an OFF frequency interval of the OFF frequencies.

7. The method of claim 6, wherein one of the ON frequencies and one of the OFF frequencies represent a binary bit, wherein the encoded data comprises at least two binary bits which represent a binary bit sequence.

8. The method of claim 6, wherein each ON frequency in the sequence is separated by an OFF frequency.

9. The method of claim 1, wherein the mechanical signal generator is an electro-mechanical stimulator, an electro-magnetic stimulator, or a piezo-electric stimulator, and wherein the receiver device is an accelerometer.

10. The method of claim 1, further comprising:
decoding, by the receiver device, the encoded data of the engineered mechanical signal.

11. A system for intra-body communication in a mammal comprising:
a mechanical signal generator device coupled to a body of the mammal; and
a receiver device coupled to the body of the mammal,
wherein the mechanical signal generator device generates an engineered mechanical signal that transmits through a musculoskeletal system of the mammal, wherein the receiver device detects the engineered mechanical signal, wherein the engineered mechanical signal comprises encoded data, wherein error compensation is applied to the detected engineered mechanical signal.

12. The system of claim 11, further comprising:
a computer program which i) encodes raw bits of data into the encoded data and ii) controls an input voltage of the mechanical signal generator device to generate the engineered mechanical signal comprising the encoded data.

13. The system of claim 11, wherein the mechanical signal generator device is an electro-mechanical stimulator, an electro-magnetic stimulator, a piezoelectric stimulator, or combinations thereof; and wherein the receiver device is an accelerometer.

14. The system of claim 11, wherein the mechanical signal generator device and the receiver device are each implanted inside the mammal or placed on an outer surface of the mammal.

15. The system of claim 11, further comprising:
one or more amplifiers coupled to the mechanical signal generator device or to the receiver device.

16. The system of claim 11, wherein the receiver device decodes the encoded data of the detected engineered mechanical signal.

17. The system of claim 11, wherein the encoded data comprises a sequence of ON frequencies and OFF frequencies, wherein each ON frequency is generated in an ON frequency interval, wherein the ON frequency interval defines an OFF frequency interval of the OFF frequencies.

18. The system of claim 17, wherein one of the ON frequencies and one of the OFF frequencies represent a binary bit, wherein the encoded data comprises at least two binary bits which represent a binary bit sequence.

19. The system of claim 18, wherein the error compensation is applied such that a bit error rate is less than about 10%.

20. The system of claim 11, wherein the mechanical signal generator device and the receiver device are in two-way communication.

* * * * *